United States Patent [19]

Corbiere

[11] Patent Number: 4,988,683

[45] Date of Patent: Jan. 29, 1991

[54] NEW PHARMACEUTICAL COMPOSITIONS FOR THE BUCCAL TRACT AND PROCESS FOR THEIR PREPARATION

[76] Inventor: Jerome Corbiere, 17 Rue Corbiere, 75016 Paris, France

[21] Appl. No.: 383,027

[22] Filed: Jul. 20, 1989

[30] Foreign Application Priority Data

Mar. 4, 1987 [FR] France .................. 87 02939

[51] Int. Cl.$^5$ .................. A61K 9/20; A61K 9/68; A61K 31/60
[52] U.S. Cl. .................. 514/165; 424/435; 424/440; 424/48; 514/162
[58] Field of Search .................. 514/165, 162; 424/440, 424/435, 48

[56] References Cited

U.S. PATENT DOCUMENTS

| | | | |
|---|---|---|---|
| 3,957,853 | 5/1976 | Bohvon | 560/143 |
| 4,115,579 | 9/1978 | Strubbe | 514/424 |
| 4,123,544 | 10/1978 | Kornowski et al. | 514/916 |
| 4,206,209 | 6/1980 | Kracaver | 424/234 |
| 4,226,885 | 10/1980 | Orzalesi et al. | 514/634 |
| 4,265,888 | 5/1981 | Kagitani et al. | 514/162 |
| 4,305,935 | 12/1981 | Kawashima et al. | 514/164 |
| 4,434,159 | 2/1984 | Sekine et al. | 514/808 |
| 4,806,530 | 2/1989 | Langer | 514/161 |
| 4,885,287 | 12/1989 | Hussain et al. | 514/159 |
| 4,885,288 | 12/1989 | Benjamin | 514/162 |

FOREIGN PATENT DOCUMENTS

| | | |
|---|---|---|
| 214881 | 3/1987 | European Pat. Off. . |
| 215635 | 3/1987 | European Pat. Off. . |
| 2611501 | 9/1988 | France . |
| 88/06449 | 9/1988 | PCT Int'l Appl. . |

OTHER PUBLICATIONS

Metabio, CA. 78:75877k (1973).
Maki, CA. 90:187339r (1978).
Flurent, CA. 99:133508n (1983).
Shah, CA. 105:178348u (1986).
Weithman CA: 106:162587f (1987).
Rebollo, CA. 107:39407r (1987).
Keroveris, CA. 108:215814c (1988).
Doutremepuica, CA 109:104530h (1988).

*Primary Examiner*—Shep K. Rose
*Attorney, Agent, or Firm*—Bierman & Muserlian

[57] ABSTRACT

This invention relates to the field of pharmaceutical chemistry and more precisely to the field of galenical pharmacy.

It refers to new pharmaceutical compositions intended for the buccal tract, the active ingredient of which is lysine acetylsalicylate in association or mixed with one or several excipients and/or diluents adapted to achieve a pharmaceutical form which may be sucked or chewed. A process for the production of said pharmaceutical composition is also described.

8 Claims, No Drawings

NEW PHARMACEUTICAL COMPOSITIONS FOR THE BUCCAL TRACT AND PROCESS FOR THEIR PREPARATION

PRIOR ART

The prior art may be best illustrated by the following references:

"Dictionnaire Vidal", 62nd edition, 1986, OVP (Paris, FR), see page 119, "Aspégic 1000".

FR, A, 2336123 (LIFE SAVERS) 22 July 1977, see page 4, example 4.

U.S. Pat. No. 4,206,209 (KRACAUER) 3 June 1980, see the whole document.

PREFERRED EMBODIMENTS OF THIS INVENTION

This invention relates to pharmaceutical compositions intended to alleviate or suppress pain and hyperthermia as well as a process for preparing the same.

More particularly it relates to analgetic and antipyretic pharmaceutical compositions intended to be sucked or chewed and the efflorescence of which is protracted.

Specifically the subject matter of this invention provides pharmaceutical compositions intended for the buccal way, in the form of tablets or lozenges to be sucked or gums to be chewed, characterized in that they contain as active ingredient lysine Acetylsalicylate in admixture or association with one or several excipients or diluents suitable for the realization of a pharmaceutical form appropriate for to be sucked or chewed.

Preferably the pharmaceutical composition according to this invention are offered in the form of tablets or lozenges, the efflorescence of which in the buccal cavity is progressive and protracted.

Among the suitable excipients or diluents, it may particularly cited buffering agents such as urea or glycine, unreactive flavouring agents and bulk agents such or mannitol or sorbitol, adhering agents with low speed of dissolution such as alkyl cellulose, for example methyl cellulose, ethylcellulose, hydroxypropyl cellulose, hydroxypropyl methyl cellulose or carboxy methyl cellulose or copolymers of methacrylic - and acrylic acid; binding agents such as polyvinyl pyrrolidone, arabic gum, guar gum, adraganth gum, karaya gum, inert diluents such as lactose, calcium carbonate, magnesium phosphate or calcium sulphate; skim milk powder, sodium caseinate; sweetening agents such as calcium saccharinate, ammonium cyclamate, ammonium glycirhizinate or Aspartame, lubricating agent such as Magnesium stearate, flavouring matters such as furaneol, maltol, isomaltol, vanillin, ethyl vanillin, or natural flavours on an inert support such as silica, lactose or arabic gum, colouring matters such as Napthol Yellow or erythrosin.

The active ingredient is Lysine acetyl salicylate. It may be as well DL-lysine acetyl salicylate, L-lysine Acetyl salicylate or D-lysine Acetyl salicylate or mixture of said salts. Preferably the product utilized is DL-lysine or L-lysine Acetyl salicylate. This active ingredient is a known compound, already utilized in the form of powders, packed in sachets, freely soluble in water and practically devoid of taste at the diluted state.

Lysine Acetyl salicylates are in the form of a finely divided white crystalline powder, hygroscopic, easily soluble in water, very slightly soluble in ethanol and in ether.

DL-lysine Acetyl salicylate melts at about 199° C. (instantaneous melting). In contrast of this, the compound previously designated as lysine mono-acetyl salicylate in the french patent 1.295.304 has a melting point determined on the Maquenne's Block of 154° -156°.

This active ingredient is somewhat unstable and associates in its molecule, a weak acid easily hydrolysed and a basic amino acid which may lead to unwanted chemical side-reactions.

In particular it may be necessary to add. to the compositions a buffering agent such as glycine which may avoid the hydrolytic reactions of the acetyl group. It has been stated that the tabletting of the tablets of Lysine Acetyl salicylate without buffering agent leads to the formation of $\alpha$-N-acetyl lysine, of 2-N-acetyl lysine and of $\alpha$, $\epsilon$-diacetyl lysine. This reaction is of the autocatalytic type. The presence of a buffering agent is of nature to avoid or at least to curb this reaction.

Moreover the presence of lysine in the molecule of the active ingredient includes the risks of a Maillard's Reaction with the sugars present in the formulation, and giving rise to the formation of strongly coloured matters, most frequently brown. It appears then as necessary to perform the realization of the formulation without any adjunction of reducing sugars such as glucose which may react with lysine and to replace them either by non-reducing sugars, i.e. sugars without a free aldehydic rest, either with glucitols such as inositol, mannitol, sorbitol or dulcitol which are unreactive toward the amino group of lysine. The pharmaceutical compositions according to this invention are intended to prepare a form which progressively release the said active ingredient in the buccal cavity where it is about totally resorbed. Pharmaceutical formulation endowed with antalgic and antipyretic, properties are more efficient due to the fact they insure higher blood levels of salicylic acid than the usual formulations.

The pharmaceutical compositions according to this invention contain an amount of lysine AcetYl salicylate-based on the amount of acetylsalicylic acid-ranging from 200 to 600 mg per unit dosage i.e. from 360 to 1080 mg of lysine acetyl salicylate. In a preferred manner the amount of lysine acetyl salicylate-based on the amount of Acetylsalicylic acid-ranges from 250 to 500 mg-i.e. 450 to 900 mg lysine Acetylsalicylate.

This invention also extend to a process for preparing the pharmaceutical compositions according to this invention - which consists in the mixing or conjunction of the active ingredient with one or several diluents, excipients, sticking agents, buffering agents, bulk agents, lubrificating agents, and/or flavouring agents, to realize a .pharmaceutical form suitable to be suckled or chewed, such as tablets, lozenges, or gums. This production is obtained according to the known methods of the pharmacotechny.

The following examples are merely illustrative of the invention without limiting it in any manner.

EXAMPLE I

Tablets to be sucked

| | |
|---|---|
| DL lysine acetyl salicylate | 720 g |
| glycine | 80 g |
| sorbitol for direct tabletting, sold under the Trade name of Neosorb 60 | 660 g |
| palatinite | 1259 g |

-continued

| | |
|---|---|
| Magnesium stearate | 45 g |
| aspartame | 4,2 g |
| for 1000 tablets achieved at the mean weight of 2,80 g | |

Palatinite is the Trade Name for an equimolar mixture of isomers of α-D-glucopyranosido, 1,6-mannitol and of α-D-glucopyranosido 1,6-glucitol, crystallized with 2 moles water.

EXAMPLE II

Tablets to be sucked

| | |
|---|---|
| DL-lysine Acetyl salicylate | 810 g |
| Glycine | 36 g |
| Ethylcellulose | 145 g |
| Magnesium Phosphate for direct tabletting | 2050 g |
| Polyvinyl pyrolidone (molecular weight higher than 30.000) | 20 g |
| Magnesium stearate | 25 g |
| Talc | 25 g |
| Calcium saccharinate | 1 g |
| Flavour orange | |
| enough for 1000 tablets achieved at the mean weight of 3,10 g | |

EXAMPLE III gum to be chewed

They are cautiously mixed together 85 g hydroxy propyl cellulose the viscosity of which determined at 20° C. on a 2 % aqueous solution, is about 2080 cp and the mean diameter of particles of which is 0,25 mm, 15 g of a copolymer of acrylic acid sold under the Trade Mark Carpopol 930 (compound substantially constituted with a copolymer of acrylic acid and allyl saccharose) then 110 g calcium phosphate, 140 g palatinite and finally 725 g lysine Acetylsalicylate. Once the mixture perfectly homogeneized, 5 g Magnesium stearate and 15 g Talc are added thereto then enough peppermint oil. The powder is screened then tabletted by direct compression into tablets having a diameter of 10 mm, a thickness of 1,1 mm, a mean weight of about 1100 mg and a hardness of 5.6 kg.

These tablets show a good geometric stability. They swell into an expansed form, pratically equal to that of the starting tablet. They progressively and completely release the active ingredient when in contact with saliva in the mouth.

EXAMPLE IV

Determination of the bioavailability of the compositions according to this invention.

The salicylhemia is determined on a group of healtly volunteers which received a solution made of 900 mg lysine acetyl salicylate-using the preparation presently on the market which has previously been dissolved in 90 ml water. Each subject keep this solution for 4 mn in his buccal cavity. The dosage of salicylhemia is performed 10 mn later. It shows a level of less than 4 mg/1. This level is very weak.

In the same subjects, the determination of the salicylhemia was carried out after administration of the tablets according to this invention.

These volunteers have to retain the tablets for 4 mn in the mouth. The salicylhemia is determined 10 mn later then 30 mn after this administration. The resulting values are more than 10 times higher than that obtained after ingestion of a solution of lysine acetylsalicylate.

What is claimed is:

1. A method of treating pain and hyperthermia in patients comprising administering buccally an amount of lysine acetylsalicylate sufficient to treat pain and hyperthermia.

2. A buccal composition for treating pain and hyperthermia comprising an effective amount of lysine acetylsalicylate and at least one buccal excipient.

3. The composition of claim 2 wherein the lysine acetylsalicylate is in the DL form.

4. The composition of claim 2 in the form of a lozenge.

5. The composition of claim 2 in the form of a chewing gum.

6. The composition of claim 2 wherein the excipient is at least one member of the group consisting of buffering agents and flavoring agents.

7. The composition of claim 2 containing 360 to 1,080 mg of lysine acetylsalicylate.

8. The composition of claim 2 containing 640 to 810 mg of lysine salicylate.

* * * * *